(12) United States Patent
Yao et al.

(10) Patent No.: US 9,284,535 B2
(45) Date of Patent: Mar. 15, 2016

(54) **METHOD FOR PRODUCING LACCASE BY MEANS OF LIQUID FERMENTATION OF *LENTINUS EDODES***

(71) Applicant: INSTITUTE OF AGRICULTURAL RESOURCES AND ENVIRONMENT, SHANDONG ACADEMY OF AGRICULTURAL SCIENCES, Jinan (CN)

(72) Inventors: Qiang Yao, Jinan (CN); Zhiyuan Gong, Jinan (CN); Zhaohui Liu, Jinan (CN); Jiandong Han, Jinan (CN); Qi Wang, Jinan (CN); Xiao Liu, Jinan (CN); Luchang Wan, Jinan (CN); Pengfei Ren, Jinan (CN); Haixia Ren, Jinan (CN); Jin Li, Jinan (CN); Peng Yang, Jinan (CN); Tao Sun, Jinan (CN)

(73) Assignee: INSTITUTE OF AGRICULTURAL RESOURCES AND ENVIRONMENT, SHANDONG ACADEMY OF AGRICULTURAL SCIENCES, Jinan (CN)

( * ) Notice: Subject to any disclaimer, the term of this patent is extended or adjusted under 35 U.S.C. 154(b) by 115 days.

(21) Appl. No.: 14/373,155

(22) PCT Filed: Mar. 22, 2013

(86) PCT No.: PCT/CN2013/000334
§ 371 (c)(1),
(2) Date: Jul. 18, 2014

(87) PCT Pub. No.: WO2013/155863
PCT Pub. Date: Oct. 24, 2013

(65) Prior Publication Data
US 2014/0363874 A1 Dec. 11, 2014

(30) Foreign Application Priority Data
Apr. 16, 2012 (CN) .......................... 2012 1 0111263

(51) Int. Cl.
*C12N 9/02* (2006.01)
*C12N 1/14* (2006.01)

(52) U.S. Cl.
CPC ................ *C12N 9/0061* (2013.01); *C12N 1/14* (2013.01)

(58) Field of Classification Search
None
See application file for complete search history.

(56) References Cited

PUBLICATIONS

Nagai et al. Purification and characterization of an extracellular laccase from the edible mushroom Lentinula edodes, and decolorization of chemically different dyes. Appl Microbiol Biotechnol 2002, vol. 60, pp. 327-335.*

* cited by examiner

*Primary Examiner* — Louise W Humphrey
*Assistant Examiner* — Christopher Keller
(74) *Attorney, Agent, or Firm* — CBM Patent Consulting, LLC

(57) ABSTRACT

A method for producing laccase by liquid fermentation of *Lentinus edodes* comprises the following steps of: (1) inoculating strains of *Lentinus edodes* into the PD liquid fermentation medium to perform activation culture and obtain a seed liquid; (2) inoculating the seed solution into a liquid fermentation medium to perform liquid fermentation culture, then adding an expansin solution to perform further culture, separating the supernatant to obtain a ferment solution; (3) extracting laccase from the ferment solution. A plant expansin and an optimized fermentation method are applied for producing laccase by liquid fermentation of *Lentinus edodes*, which increases the liquid fermentation output of laccase of *Lentinus edodes* remarkably, by more than 3 times in comparing with traditional fermentation production methods.

8 Claims, No Drawings

METHOD FOR PRODUCING LACCASE BY MEANS OF LIQUID FERMENTATION OF *LENTINUS EDODES*

This application is the U.S. national phase of International Application No. PCT/CN2013/000334 Filed on 22 Mar. 2013 which designated the U.S. and claims priority to Chinese Application Nos. 201210111263.0 filed on 16 Apr. 2012, the entire contents of each of which are hereby incorporated by reference.

TECHNICAL FIELD

The invention relates to a method for producing laccase, an industrial enzyme agent, by liquid fermentation of *Lentinus edodes*, which belongs to biotechnology fermentation engineering field.

BACKGROUND

The laccase (P-diphenol oxidase, EC 1.10.3.2) is a multi-copper-binding protein, belonging to coveline oxidoase, which may be derived from fungi (e.g. mushrooms), bacteria and plants, especially presented widely in white rot fungi of basidiomycetes. Laccase can be lived in the air, and is a environment-friendly ferment whose sole product is water after reaction. Due to recognizing environment protection gradually, recently laccase is hot point at home and abroad. Fungi laccases have four copper ion in general, so its electric levels of oxidation and deoxidization is higher than laccase from insects and plants. The laccase can oxidize several kinds of hydroxybenzene, arylamine, carboxylic acid, steroid hormone, biochrome, metallorganic compound and some non-phenolic substrates. So it can be applied widely in several modern industrial fields such as waste water treatment, paper pulp blanching, soil cleansing, dye decoloring, immunity detection, etc. *Lentinus edodus* (*Lentinula edodes*) is also named Araricus bretschneideri Kalich et Thum, belonging to Bssidiomycetes class, Agaricales order, Mushroom family, Leather pleat L. genus, whose formal name is Fragrant leather wimple bacteria. *Lentinus edodus* has longtime history of production and cultivation in our country, where is biggest country in globe of *Lentinus edodes* production. Now *Lentinus edodus* have been cultivated in more than 70% of provinces of our country. So *Lentinus edodus* has some characters such as low price, more producing areas, easily cultivation. As a kind of white rot fungi, *Lentinus edodus* has been proved that it can be used to produce laccase, which includes several kinds of isoenzyme and is collectively named by total laccase. And the activity of oxidation and deoxidization of the laccase is also much higher than that of the laccase from insects or plants. Comparing with extracting directly from *Lentinus edodus* sporophore, liquid fermentation technology with low cost and higher efficiency is presently the developing direction of industrial fermentation production. However, there is too few researches related to *Lentinus edodus* fermentation to produce laccase by now. The yield of *Lentinus edodus* laccase is still lower than that of other active components of *Lentinus edodus* by fermentation and extract. And the enzyme activity of laccase is restricted by many factors such as culture conditions and substrate components. It has been reported that some Aromatic compounds or heavy metal ion may be used to induce and increase the outputs, but these inducer are commonly toxic and difficult to degrade. After adding these inducer, the cost of treating fermentation liquid is increasing and the environment is also easily polluted. Using static liquid culturing or solid fermentation technologies may relieve the problem of environment pollution of laccase production, but the fermentation period is too long, which is not suitable for industrial fermentation production.

Chinese patent CN1463578A (application No. 02124094) discloses one kind of deep fermentation method of culturing liquid *Lentinus edodes* seed and its culture medium. The culture method includes the steps of: (1) performing mother seed culture in a mother seed culture medium; (2) transferring the mycelia overgrowing in the mother seed medium of the tubes to original sawdust culture medium for transitional culturing at temperature 22~27±1° C. for 12~20 days in dark until mycelium overgrowing; (3) transferring the fully crushed sawdust seed immediately to the liquid culture medium for amplification in the first shake flask; (4) transferring the liquid culture cultured for 5-7 days in the first shake flask to the second shake flask with fresh liquid culture medium for amplification; (5) and treating the liquid culture cultured in the second shake flask by fermentation to obtain liquid *Lentinus edodus* seed product. The yields using other laccase gene for heterogenous expression are lower than wild type. These factors limit the industrial production and application of laccase. So it is much needed to develop a new preparation method and production process of increasing production ratio of laccase and decreasing production cost to satisfy modern industry.

Recently a new type of protein named expansin is found in plant cell walls. Studies have shown that expansin plays an very important role in several aspects such as plant morphogenesis (Fleming et al., 1999), fruit ripening (Cosgrove, 2000), root hair formation (Cho and Cosgrove, 2002), cell expanding (Cosgrove, 1998), penetration regulation (Wu and Cosgrove, 2000) and pollen tube growth of graminaceous plants (Cosgrove, 1997), etc. Expansin has been found in *Arabidopsis*, tomato, strawberry, cotton, rice, corn and other plants, and is considered existing in various dicotyledonous and monocotyledonous plant cell walls. Experiments have shown that as a plant cell wall protein, expansin has the function of recovering the thermal inactivated cell wall to extend in vitro. Therefore, it is supposed that expansin can regulate physiological activities such as acid-dependent cell wall extension and stress relaxation by breaking the hydrogen bonds between the cell wall polymers, and may play regulation functions such as physiological regulation and cell wall extension process in the period of plant growth. However, the mechanism of expansin is not yet a clear conclusion. Currently it is not reported at home and abroad that the expansin is applied in liquid fermentation of *Lentinus edodes* to produce secondary metabolites such as laccase.

SUMMARY OF THE INVENTION

In view of the defects of the prior art, the present invention aim to provide a method using liquid fermentation of *Lentinus edodus* to produce laccase.

The technical scheme of the present invention is as follows:

A method for producing laccase by liquid fermentation of *Lentinus edodes*, comprises the following steps of:

(1) inoculating strains of *Lentinus edodes* into the PD liquid fermentation medium to perform activation culture and obtain a seed liquid;

(2) inoculating the seed liquid obtained in the step (1) into a liquid fermentation medium by a volume ratio of 5~15% to perform liquid fermentation culture at temperature 25~30° C. for 1~5 days, then adding an expansin solution to a concentration of 1.0~3.0 mg/mL to perform further culture for 4~8 days, separating the supernatant to obtain a ferment solution;

(3) extracting laccase from the ferment solution obtained in the step (2).

Preferably, according to the invention, per liter of the PD liquid fermentation medium in the step (1) comprises the following components:

peeled potato 200 g, glucose 20 g, dilute to 1000 mL by distilled water.

According to the invention, the preferred activation culture in the step (1) is processed with a shaking speed of 100~180 r/min at 25~30° C. for 3~6 days.

Preferably, according to the invention, the liquid fermentation medium in the step (2) has a pH of 5.0~7.0, and per liter comprises the following components:

corn powder 100 g, bran 100 g, sucrose 20 g, white sugar 10 g, peptone 2 g, $MgSO_4.7H_2O$ 0.5 g, $KH_2PO_4$ 0.5 g, diluted by water to 1000 ml.

Preferably, according to the invention, the expansin concentration in the step (2) is 1.5~3.0 mg/mL; further preferably, 2.0~3.0 mg/mL. Most preferably, the expansin concentration in the step (2) is 2.5 mg/mL.

The preparation of the expansin protein solution in the step (2) may refer to the prior technique, such as the method described in "Two endogenous proteins that induce cell wall extension in plants. McQueen-Mason et al. Plant Cell, 1992, 4: 1425~1433. McQueen-Mason S J, Durachko D M, Cosgrove D J". The expansin protein solution in step (2) may also be prepared by the method which comprises the following steps of:

sterilizing a broad bean or cucumber seed for 4~6 minutes with 0.05~0.15 wt. % mercury chloride ($HgCl_2$), washing with running water for 5~7 hours, culturing in the darkroom for 4~6 days at 15~28° C., taking 3~4 cm of seedling hypocotyl apices, precooling for 0.5 hours at −20° C., adding a homogenate buffer solution that is pre-cooled to 4° C., filtering with a nylon net having an aperture of 70 μm after homogenate, washing the filter residue with a homogenate buffer solution, adding the filter residue in the homogenate buffer solution, settling for 1~3 hours to obtain a settled solution, adding an extracting solution in the settled solution, extracting for 44~50 hours at 4° C., slowly adding 0.3~0.5 g/mL ammonium sulfate (($NH_4)_2SO_4$) in the filtrate while stirring to prevent a partial supersaturation of the ($NH_4)_2SO_4$, settling for 25~30 hours, centrifuging for 5~10 minutes at 4° C., dissolving the sediment with an acid buffer solution, dialyzing in a dialysis bag with a molecular weight of 3000 Da at 4° C., centrifuging the dialyzate at 20000 g for 10 minutes, and taking the supernatant so as to obtain the expansin protein solution.

In the above preparation method of the expansin protein solution, the homogenate buffer solution has a pH of 7.0, and comprises 25 mmol/L HEPES (4-(2-hydroxyethyl)-1-piperazineethanesulfonic acid), 1.5 mmol/L $Na_2S_2O_5$, 2 mmol/L EDTA and 0.1 wt. % Triton X-100. The extracting solution has a pH of 6.0, and comprises 15 mmol/L 4-(2-hydroxyethyl)-1-piperazineethanesulfonic acid, 1.0 mmol/L EDTA, 1.5 mmol/L $Na_2S_2O_5$ and 0.5 mmol/L NaCl. The acid buffer solution is prepared by dissolving 2.05 g of sodium acetate in water, adjusting pH to 4.0 with glacial acetic acid, and adding water to 1 L.

Preferably, according to the invention, the separation in the step (2) is carried out by filtrating the ferment broth with 4~6 layers of gauze and centrifuging with a rotate speed of 8000 r/min at 4° C. for 15 minutes.

In the step (3), the extraction method of laccase from the ferment solution comprises the following steps of:

adding grinded ammonium sulfate (($NH_4)_2SO_4$) into the ferment solution obtained in the step (2) at 0~4° C. to 0.3~0.5 g/mL, adding while stirring to prevent a partial supersaturation of ammonium sulfate (($NH_4)_2SO_4$), static settling at 4° C. for 6~8 hours, 10000 rpm centrifuging for 20 minutes at 4° C., discarding the supernatant, dissolving the precipitate into sodium hydrogen phosphate-citrate buffer; dialyzing in a dialysis bag with a molecular weight of 10~20 kDa at 4° C., ultrafiltrating and concentrating by a dialysis membrane with a molecular weight of 10~20 kDa at 4° C., removing small molecule proteins so as to obtain *Lentinus edodes* laccase solution.

The sodium hydrogen phosphate-citrate buffer has a pH of 8.0, and is prepared by dissolving 0.69 g sodium dihydrogen phosphate, 0.012 g citric acid in distilled water and diluting to 1 L.

Compared with the prior art, the present invention has the following advantages:

1. Plant expansin and optimized fermentation process is applied in the method of the present invention for producing laccase of *Lentinus edodes* by liquid fermentation, therefore the yield of laccase of *Lentinus edodes* by liquid fermentation is significantly increased to 17.41 U/mL, which is more than 3.2 times of the yield made by traditional fermentation methods. The method has an excellent industrial application prospect.

2. The liquid fermentation method of *Lentinus edodes* in the present invention is simple, environment-friendly, non-toxic and low raw material costs. The whole fermentation process is easily controlled and not restricted by external environmental conditions, so it is ideal for fermentor production in industrial-scale. The method is also applicable to other cultivars of common *Lentinus edodes*.

3. The expansin mentioned in the invention can be extracted from most dicotyledonous and monocotyledonous plants, which is widely-available and low-cost. The preparation method is relatively simple and well repeatable, thus it can be applied for extraction in industrial scale.

Embodiment

The following is the detail description of the present invention with reference to examples, but the scope of the present invention is not limited thereto.

Raw Materials and Medium

The fermentation strain described in Examples is *Lentinus edodes*, with Culture Collection No. of XDJ-1, purchased from Jinan Xiandao Biotechnology Co., Ltd.

The dialysis bag of polyvinylidene fluoride (PVDF) with cutoff molecular weight of 10~20 kDa was purchased from Beijing Borunlaite Biotechnology Co., Ltd. The dialysis film of POLYVINYLIDENE FLUORIDE (PVDF) with cutoff molecular weight of 10~20 kDa was purchased from Jinan Shengwei Biotechnology Co., Ltd.

Standard solution of cattle blood serum protein, Coomassie brilliant blue and guaiacol were purchased from Jinan Shengwei Biotechnology Co., Ltd. Other reagents are all conventional commercial products.

The expansin protein solution of examples can be prepared by the method which comprises the following steps of:

sterilizing the soybean (*Glycine max L. Merr*. CV. M40; purchased from Jinan Weili Seed Industry Co., Ltd) or cucumber seed (*Cucumis sativus L*. CV Jinnian No 6; purchased from Jinan Weili Seed Industry Co., Ltd.) with 0.1 wt % $HgCl_2$ for 5 minutes, washing with running water for 6 h, planting in wet vermiculite, dark culturing for 4 days at 27° C., taking 3~4 cm of seedling hypocotyl apices, e.g. growing area that about 100 g, setting at −20° C. for 0.5 hour to pre-cool, adding homogenate buffer solution that pre-cooled to 4° C., filtering with a nylon net having an aperture of 70 μm after high speed dividing, washing the filter residue with homogenate buffer solution, adding the filter residue in the homogenate buffer solution, settling for 2 hours to obtain a settled solution, adding an extracting solution in the settled solution, extracting for 48 hours at 4° C., slowly adding 0.4 g/mL ammonium sulfate (($NH_4$)$_2SO_4$) in the filtrate while stirring to prevent a partial supersaturation of the ($NH_4$)$_2SO_4$, settling for 28 hours, centrifuging at 25000 g at 4° C. for 10 minutes, dissolving the sediment with an acid buffer solution, dialyzing in a polyvinylidene fluoride (PVDF) dialysis bag (purchased from Beijing Lubrizol Wright Science and Technology Co., Ltd.) with a molecular weight of 3000 Da at 4° C., centrifuging at 20000 g the dialyzate for 10 minutes, taking the supernatant so as to obtain the expansin protein solution and reserving at 4° C. Other steps that are not described can consult the descriptions in "Two endogenous proteins that induce cell wall extension in plants. McQueen-Mason et al. Plant Cell, 1992, 4: 1425~1433. McQueen-Mason S J, Durachko D M, Cosgrove D J".

The homogenate buffer solution mentioned as above has a pH of 7.0, and comprises 25 mmol/L HEPES (4-(2-hydroxyethyl)-1-piperazineethanesulfonic acid), 1.5 mmol/L $Na_2S_2O_5$, 2 mmol/L EDTA and 0.1 wt. % Triton X-100.

The extracting solution has a pH of 6.0, and comprises 15 mmol/L 4-(2-hydroxyethyl)-1-piperazineethanesulfonic acid, 1.0 mmol/L EDTA, 1.5 mmol/L $Na_2S_2O_5$ and 0.5 mmol/L NaCl.

The acid buffer solution is prepared by dissolving 2.05 g of sodium acetate in water, adjusting pH to 4.0 with glacial acetic acid, and adding water to 1 L.

The concentration determination of the expansin protein solution can employ Coomassie brilliant blue method, which may specifically refer to the operations of Coomassie blue method described in "Quintessence of Protein Science Laboratory Manual" (ISBN: 703018086, publication date: 1900-1-1), by using bovine serum albumin as the standard curve. The expansin concentration of the expansin protein solution detected by the above method and the result is 0.31 g/mL.

Per liter of the PD liquid fermentation medium described in examples comprises the following components: peeled potato 200 g, glucose 20 g, dilute to 1000 mL by distilled water.

The liquid fermentation medium in the examples has a pH of 5.0~7.0, and per liter comprises the following components: corn powder 100 g, bran 100 g, sucrose 20 g, white sugar 10 g, peptone 2 g, $MgSO_4 \cdot 7H_2O$ 0.5 g, $KH_2PO_4$ 0.5 g, diluted by water to 1000 ml.

The sodium hydrogen phosphate-citrate buffer mentioned in the examples has a pH of 8.0, and is prepared by dissolving 0.69 g sodium dihydrogen phosphate, 0.012 g citric acid in distilled water and diluting to 1 L.

The sodium succinate buffer mentioned in the examples is prepared by taking 1.0 g sodium hydroxide and 5.9 g succinic acid to dissolve in 800 mL distilled water, then adjusting to pH 4.5 by sodium hydroxide solution and diluting by distilled water to 1000 mL.

EXAMPLE 1

A method for producing laccase by liquid fermentation of *Lentinus edodes*, comprises the following steps of:

(1) inoculating *Lentinus edodes* strains which has a strain number of XDJ-1 into the PD liquid fermentation medium to perform activation culture with a shaking speed of 150 r/min at 28° C. for 3 days, and obtain a seed liquid;

(2) inoculating the seed liquid obtained in the step (1) into a liquid fermentation medium by a volume ratio of 10% to perform liquid fermentation culture at temperature 25° C. for 1 days, then adding an expansin solution to a concentration of 1.5 mg/mL to perform further culture for 8 days, filtrating with 5 layers of gauze and centrifuging with a rotate speed of 8000 r/min at 4° C. for 15 minutes to separate the supernatant and obtain a ferment solution;

(3) slowly adding grinded ammonium sulfate (($NH_4$)$_2SO_4$) into the ferment solution to 0.4 g/mL at 4° C. while stirring to prevent a partial supersaturation of ammonium sulfate (($NH_4$)$_2SO_4$), static settling at 4° C. for 8 hours, centrifuging with a rotate speed of 10000 rpm for 20 minutes at 4° C., discarding the supernatant, dissolving the precipitate into sodium hydrogen phosphate-citrate buffer; dialyzing in a dialysis bag with a molecular weight of 10~20 kDa at 4° C., ultrafiltrating and concentrating by a dialysis membrane with a molecular weight of 10~20 kDa at 4° C., removing small molecule proteins so as to obtain *Lentinus edodes* laccase solution.

Preparation of Laccase Samples

The laccase produced from 1 L ferment solution is diluted by sodium hydrogen phosphate-citrate buffer to 50 mL to obtain the laccase sample.

Determination of Laccase content (1) Establishment of Standard Curve:

Conventional BCA method in the art may be used, which can be referred to "Protein Technology Manual. ISBN: 7-03-008329-6, published date: 2000".

The standard curve can be built by the method which comprises the following steps of: setting 0.0 mL, 0.1 mL, 0.2 mL, 0.3 mL, 0.4 mL, 0.5 mL, 0.6 mL standard solution (0.5 g/L) of cattle blood serum protein into tubes, separately adding 1.0 mL, 0.9 mL, 0.8 mL, 0.7 mL, 0.6 mL, 0.5 mL, 0.4 mL of 0.15 mol/L NaCl solution, then separately added 5 mL of 0.01% (W/V) Coomassie brilliant blue, mensurating OD value by spectrophotometer at 465 nm to obtain the standard curve.

(2) Determination of the Yield of Laccase:

The yield of laccase is determined by the method which comprises the following steps of: taking 10 μL laccase sample into tubes, diluting to 1 L with 0.15 mol/L NaCl solution and shaking to uniform, then adding 5 mL of 0.01% (W/V) Coomassie brilliant blue, mensurating OD value by spectrophotometer at 465 nm. The blank control is 1.0 mL of 0.15 mol/L NaCl solution. According to the standard curve, we can calculate the content of protein and the result is 0.234 g/L. The total protein content of crude laccase per liter ferment solution is: 0.234×100/20=1.17 g.

(3) Determination of Laccase Activity:

Conventional Guaiacol method in the art (referred to "Yurong Zhang, et al. Effect factors of guaiacol method to determine the activity of maize peroxidase. Food Engineering. 2008: 4~7") may be used to determine total activity of laccase from ferment solution.

The determination process comprises the following steps of: mixing 1 mL of sodium succinate buffer, 1 mL of 4 mM guaiacol and 0.5 mL of laccase sample to obtain 2.5 mL solution, reacting at 30° C. for 30 minutes, then measuring absorbency value by spectrophotometer at 465 nm. The blank control was made by mixing 1 mL sodium succinate buffer, 1 mL of 4 mM guaiacol and 0.5 ml sodium hydrogen phosphate-citrate buffer instead of laccase samplev.

The definition of enzyme activity units of laccase mentioned as above: one enzyme activity unit (U) is that can change $OD_{465}$ value by 0.01 per minute.

After detecting, the total enzyme activity of laccase sample is 85.1 U. Then we can calculate the total enzyme activity of crude laccase per liter ferment solution is 85.1×2/20=8.51 U (multiplying detected value with 2 to obtain enzyme activity per ml, then dividing by concentration multiple of ferment solution). The result is shown in Table 1.

EXAMPLE 2

It is the same as the method described in Example 1, except that in the step (2) the expansin protein solution is added to a concentration of 2.0 mg/mL after liquid fermentation culture at 25° C. for 3 days, and performed further culture for 6 days.

After been detected and calculated, the total protein content per liter crude laccase from the ferment solution is 1.52 g, and the total enzyme activity of crude laccase per milliliter ferment solution is 10.33 U. The result is shown in Table 1.

EXAMPLE 3

It is the same as the method described in Example 1, except that in the step (2) the expansin protein solution is added to a concentration of 2.5 mg/mL after liquid fermentation culture at 25° C. for 5 days, and performed further culture for 4 days.

After been detected and calculated, the total protein content per liter crude laccase from the ferment solution is 2.82 g, and the total enzyme activity of crude laccase per milliliter ferment solution is 17.41 U. The result is shown in Table 1.

COMPARATIVE EXAMPLE 1

It is the same as the method described in Example 1, except that in the step (2) the seed liquid obtained in the step (1) is inoculated by a volume ratio of 10% into the liquid ferment medium to perform liquid fermentation culture at 25° C. for 9 days and filtrate to obtain the ferment solution.

After been detected and calculated, the total protein content per liter crude laccase from the ferment solution is 0.71 g, and the total enzyme activity of crude laccase per milliliter ferment solution is 4.07 U. The result is shown in Table 1.

TABLE 1

Comparison of yield of *Lentinus edodes* laccase in different examples

| embodiment | Concentration of expansin (mg/mL) | Adding time (d) | Total protein (g/L) | Total activity of laccase (U/mL) |
|---|---|---|---|---|
| Example 1 | 1.5 | 1 | 1.17 | 8.51 |
| Example 2 | 2.0 | 3 | 1.52 | 10.33 |
| Example 3 | 2.5 | 5 | 2.82 | 17.41 |
| Comparative Example 1 | — | — | 0.71 | 4.07 |

What is claimed is:

1. A method for producing laccase by liquid fermentation of *Lentinus edodes*, comprises the following steps of:
   (1) inoculating *Lentinus edodes* into a potato dextrose (PD) liquid fermentation medium comprising 200 g peeled potato, 20 g glucose and 1000 ml water to perform activation culture to obtain a seed liquid;
   preparing an expansin solution by sterilizing a broad bean or cucumber seed with mercury chloride ($HgCl_2$) for 4 to 6 minutes, washing with running water for 5 to 7 hours, culturing in the darkroom for 4 to 6 days at the temperature between 15 and 28° C.; precooling seedling hypocotyl apices for 0.5 hours at −20° C., adding a homogenate buffer solution that is pre-cooled to 4° C., filtering with a nylon net having an aperture of 70 μm after homogenate, washing the filter residue with a homogenate buffer solution, adding the filter residue in the homogenate buffer solution, settling for 1 to 3 hours to obtain a settled solution, adding an extracting solution in the settled solution for 44 to 50 hours at 4° C., adding 0.3 to 0 5g/ml of ammonium sulfate (($NH_4)_2SO_4$) in the filtrate while stirring to prevent a partial supersaturation of the ($NH_4)_2SO_4$, settling for 25 to 30 hours, centrifuging for 5 to 10 minutes at 4° C., dissolving the sediment with an acid buffer solution, dialyzing in a dialysis bag with a molecular weight of 3000 Da at 4° C., centrifuging the dialysate at 20000 g for 10 minutes, and taking the supernatant to obtain the expansin solution;
   (2) inoculating the seed liquid into a liquid fermentation medium for liquid fermentation culture at a temperature between 25 and 30° C. for 1 to 5 days, then adding the expansin solution at a concentration of 1.0~3.0 mg/ml for further culture for 4 to 8 days, then separating the supernatant to obtain a fermentation solution;
   (3) extracting laccase from the fermentation solution obtained in step (2), comprising: adding grinded ammonium sulfate ($NH_4)_2SO_4$ into the fermentation solution obtained in step (2) at a temperature between 0 and 4° C., settling at 4° C. for 6 to 8 hours, centrifuging with a rotation speed of 10000 rpm for 20 minutes at 4° C., discarding the supernatant, dissolving the precipitate into sodium hydrogen phosphate-citrate buffer; dialyzing in a dialysis bag with a molecular weight between 10 and 20 kDa at 4° C., ultrafiltrating and concentrating by a dialysis membrane with a molecular weight between 10 and 20 kDa at 4° C., removing small molecule proteins to obtain *Lentinus edodes* laccase solution,
   wherein the liquid fermentation medium in step (2) has a pH between 5.0 and 7.0, and contains corn powder, bran, sucrose, white sugar, peptone, $MgSO_4.7H_2O$, $KH_2PO_4$.

2. The method according to claim 1, wherein the activation culture in step (1) is processed in the darkroom with a shaking speed of 100 to 180 r/min at the temperature between 25 and 30° C. for 3 to 6 days.

3. The method according to claim 1, wherein the concentration of expansin in step (2) is between 1.5 and 3.0 mg/ml.

4. The method according to claim 3, wherein the concentration of expansin in step (2) is between 2.0 and 3.0 mg/ml.

5. The method according to claim 4, wherein the concentration of expansin in step (2) is 2.5 mg/ml.

6. The method according to claim 1, wherein the homogenate buffer solution has a pH of 7.0, and comprises 15-35 mmol/L of HEPES (4-(2-hydroxyethyl)-1-piperazineethanesulfonic acid), 0.5-2.5 mmol/L of $Na_2S_2O_5$, 1-3 mmol/L of EDTA and 0.001-0.2% Triton X-100; the extracting solution has a pH between 5-7, and comprises 10-20 mmol/L of 4-(2-hydroxyethyl)-1-piperazineethanesulfonic acid, 0.5-2 mmol/L of EDTA, 0.5-2.5 mmol/L of $Na_2S_2O_5$ and 0.1-1 mmol/L of NaCl; the acid buffer solution is prepared by dissolving sodium acetate in water, pH is adjusted to between 3 and 5 with glacial acetic acid.

7. The method according to claim 1, wherein the separation in step (2) is carried out by filtrating the fermentation broth with 4 to 6 layers of gauze and centrifuging with a rotation speed of 8000 r/min at 4° C. for 15 minutes.

8. The method according to claim 1, wherein the sodium hydrogen phosphate-citrate buffer has a pH between 7 and 9, and is prepared by dissolving sodium dihydrogen phosphate and citric acid in distilled water.

* * * * *